(12) United States Patent
Motz

(10) Patent No.: US 7,291,757 B2
(45) Date of Patent: Nov. 6, 2007

(54) METHOD AND DEVICE FOR UTILIZING HEAT IN THE PRODUCTION OF 1,2-DICHLOROETHANE

(75) Inventor: Joachim Motz, Kelkeim (DE)

(73) Assignee: UHDE GmbH, Dortmund (DE)

( * ) Notice: Subject to any disclaimer, the term of this patent is extended or adjusted under 35 U.S.C. 154(b) by 543 days.

(21) Appl. No.: 10/670,970

(22) Filed: Sep. 25, 2003

(65) Prior Publication Data

US 2004/0059166 A1   Mar. 25, 2004

Related U.S. Application Data

(63) Continuation of application No. 10/070,842, filed as application No. PCT/EP00/08963 on Sep. 14, 2000, now Pat. No. 6,693,224.

(30) Foreign Application Priority Data

Sep. 22, 1999   (DE)   ................. 199 45 355
Jul. 29, 2000   (DE)   ................. 100 37 323

(51) Int. Cl.
*C07C 17/02*   (2006.01)
*C07C 17/38*   (2006.01)

(52) U.S. Cl. ...................................................... 570/262

(58) Field of Classification Search ................. 570/262
See application file for complete search history.

(56) References Cited

FOREIGN PATENT DOCUMENTS

DE   4131576 A1 *   3/1993

* cited by examiner

*Primary Examiner*—Elvis O. Price
(74) *Attorney, Agent, or Firm*—Marshall & Melhorn, LLC

(57) ABSTRACT

The invention relates to a method for the production of 1,2-dichloroethane by direct chlorination using chlorine and ethene in which, despite low reaction temperatures during direct chlorination, reaction heat produced is nevertheless used. According to the invention, vaporous 1,2-dichloroethane obtained in the direct chlorination reactor is compressed and the compressed 1,2-dichloroethane is transported to heat exchangers whereby heat is given off by the 1,2-dichloroethane. The invention also relates directly after the direct chlorination reactor.

9 Claims, 2 Drawing Sheets

METHOD AND DEVICE FOR UTILIZING HEAT IN THE PRODUCTION OF 1,2-DICHLOROETHANE

CROSS-REFERENCE TO RELATED APPLICATIONS

This application claims continuation status from U.S. patent application Ser. No. 10/070,842, filed May 22, 2002 now U.S. Pat. No. 6,693,224, which was a 371 application off of international application PCT/EP00/08963 filed 14 Sep. 2000. U.S. patent application Ser. No. 10/070,842 was pending as of the filing date of this application. U.S. patent application Ser. No. 10/070,842 is hereby incorporated by reference as if set forth in its entirety herein.

BACKGROUND OF THE INVENTION

The invention relates to a process for the production of 1,2-dichloroethane, hereinafter referred to as "EDC", which primarily serves as an intermediate product in the production of monomer vinyl chloride, hereinafter referred to as "VCM", which, in turn, is used to produce polyvinyl chloride (PVC), and the invention also relates to a facility for running the said process.

SUMMARY OF THE INVENTION

Hydrogen chloride (HCl) is obtained when EDC is reacted to produce VCM. Hence, the preferred method of producing EDC from ethene ($C_2H_4$) and chlorine ($Cl_2$) is such that a balance is maintained between the hydrogen chloride (HCl) produced and consumed in the various reactions, which is substantiated as follows:

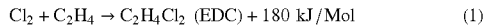

$$Cl_2 + C_2H_4 \rightarrow C_2H_4Cl_2 \text{ (EDC)} + 180 \text{ kJ/Mol} \quad (1)$$

$$C_2H_4Cl_2 \text{ (EDC)} \rightarrow C_2H_3Cl \text{ (VCM)} + HCl - 71 \text{ kJ/Mol} \quad (2)$$

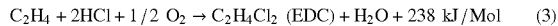

$$C_2H_4 + 2HCl + 1/2 \, O_2 \rightarrow C_2H_4Cl_2 \text{ (EDC)} + H_2O + 238 \text{ kJ/Mol} \quad (3)$$

The step of the production process that refers to reaction (1) is hereinafter called "direct chlorination", the step that refers to reaction (2) is called EDC cracking and the step that refers to reaction (3) is called oxihydrochlorination. The whole production process is hereinafter referred to as "balanced process" provided the HCl obtained by EDC cracking is completely consumed in the oxhydrochlorination unit.

Direct chlorination is usually carried out in a loop reactor which is available in various types of design. Such a process is for instance described in DE 43 18 609 A1. Many years of practical experience have shown that the purity of the EDC produced is of major importance for the cost effectiveness and the final product purity which can be achieved for the VCM obtained by reaction (2) and consequently for the complete process. This gave way to many attempts to minimise the side reactions related to reaction (1).

A very successful attempt was the reduction of the reaction temperature which, however, involved the disadvantage that the reaction heat developed at a relatively low temperature and thus could not be adequately exploited in the EDC production process. The reaction heat thus became waste heat and the specialists involved finally decided to discard this way of minimising the side reactions in connection with reaction (1).

The heat exploitation measures in the balanced process are of major economical and ecological importance. DE 41 31 576 A1, for example, describes a rather expensive method for the recovery of the heat contained in EDC vapours. The EDC feed required for an equilibrated balance is produced according to reaction (1) at temperatures ranging from 75 to 100° C., by boiling the EDC, condensing the vapours and causing the condensed vapour stream to return to the reactor, the product being withdrawn before. Another approach involved the separation of heat from the liquid EDC circulated in the reactor. The refrigeration capacity required to condense the vapours from the EDC reactor and/or the liquid EDC circulated in the reactor amounts to approx. 420 kWh per tonne of produced VCM. If liquid chlorine is used as feed product, the heating capacity required to evaporate the chlorine is 35 kWh per tonne of produced VCM.

The EDC from the oxihydrochlorination or from the direct chlorination, if any, as well as the unconverted EDC from the EDC cracking must undergo distillation, as the EDC used as feedstock for EDC cracking must be of ultrahigh purity. The distillation usually takes place in distillation columns, water and light ends being separated in a dehydration or light ends column and heavy ends being removed in one or two columns which are called heavy ends or vacuum columns. The amount of steam required to operate these distillation columns is approx. 513 kWh per tonne of produced VCM, provided the EDC from the direct chlorination and oxihydrochlorination as well as the unconverted EDC portion from the EDC cracking are distilled simultaneously. Should a distillation of the EDC from the direct chlorination not be necessary, as the reaction conditions can be adjusted such that the EDC purity required for EDC cracking is reached without distillation, the amount of steam required for treating the remaining EDC portion drops to 385 kWh per tonne of produced VCM.

Some of the processes suggested provided for the exploitation of the complete reaction heat produced in the direct chlorination by condensing the vapours from said chlorination in order to heat the heavy ends column and the vacuum column. The relatively high reaction temperature required for direct chlorination in such a case, however, reduces the yield of this type of process (referred to the feedstock chlorine and ethene) and it also deteriorates the quality of the EDC from the direct chlorination so that there is a need for an intensified distillation which adversely affects the economic efficiency.

Processes with the aim to improve the operational efficiency of columns with the aid of vapours compression have already been described. Patent FR 2 578 537 A1, for example, provides for a process using the heat released from the vapours compression inside an EDC heavy ends column for heating the bottom of said column.

Patent EP 0 131.932 A1, for example, provides for a process using the heat released from the vapours compression inside an EDC heavy ends column for heating the bottom of said column and/or for heating the light-ends column.

The above mentioned document DE 41 31 576 A1 describes a process using the vapours of heavy ends separating column for powering the bottom heating system of the dehydration column.

Patent EP 0 180 925 B1 describes another process by which vapours from the heavy ends separating column of a VCM production plant are compressed and used for heating the bottom of the column. This document also sets forth the necessity to check the system as to whether further reactions take place during the compression phase, thus causing EDC contamination or maloperation of the compressor.

In contrast to the present invention, the above mentioned technologies use the vapours from the purifying columns and not those from the direct chlorination reactor.

The aim of the process according to the invention, therefore, is to use the reaction heat obtained in the direct chlorination although the reaction temperature is low.

This aim can be achieved by a process and a facility specified in the preceding paragraphs of this invention, the vaporous EDC from the direct chlorination reactor being compressed and then piped to heat exchangers for heat recovery.

This measure has proven to be a suitable method for lowering the reaction temperature in the direct chlorination unit to a level that permits piping the EDC produced in said unit to the EDC cracking unit without any further distillative treatment, which precludes the disadvantage that reaction heat is obtained at a temperature level inappropriate for any further use of the heat. The compression will in fact raise the temperature of the compressed EDC as well as the EDC condensation temperature so that the condensed EDC can be used at a temperature higher than that of the direct chlorination.

Further embodiments of the process according to the invention can be seen in sub-claims. They provide especially for the compressed vapours to be fed to the evaporator of a light ends or dehydration column and/or the evaporator of a heavy ends column and/or the evaporator of a vacuum column and/or the chlorine evaporator upstream of the direct chlorination reactor. As the invention has the advantage that the reaction heat of 420 kWh per tonne of VCM produced in the direction chlorination unit corresponds almost exactly to the total demand of heating energy required for the operation of the distillation columns (385 kWh per tonne of produced VCM) and the chlorine evaporation (35 kWh per tonne of produced VCM), the invention provides a concept for the specialist to distribute the reaction heat among the consumers mentioned and to restrict the use of imported energy to the amount needed for plant control and for the operation of the compression unit which is an essential part of this invention.

The invention provides for a compact design of the facility according to the invention, as the compressed vapours can be used for heating the EDC column and for heating other columns provided in an embodiment of the invention. The vaporous 1,2-dichloroethane withdrawn from the direct chlorination reactor is compressed by means of a turbocompressor. In another embodiment of the invention, the turbocompressor is fitted with a shaft seal of tandem design with nitrogen as the barrier gas. In another embodiment of the invention, a speed controller serves to adjust the delivery rate of the turbocompressor to the discharge rate of the direct chlorination reactor.

BRIEF DESCRIPTION OF THE DRAWINGS

Other advantages, details and features of the invention are contained in the following description and illustrated in the enclosed diagrams.

They show the following.

DESCRIPTION OF THE PREFERRED EMBODIMENTS

Figure 1:
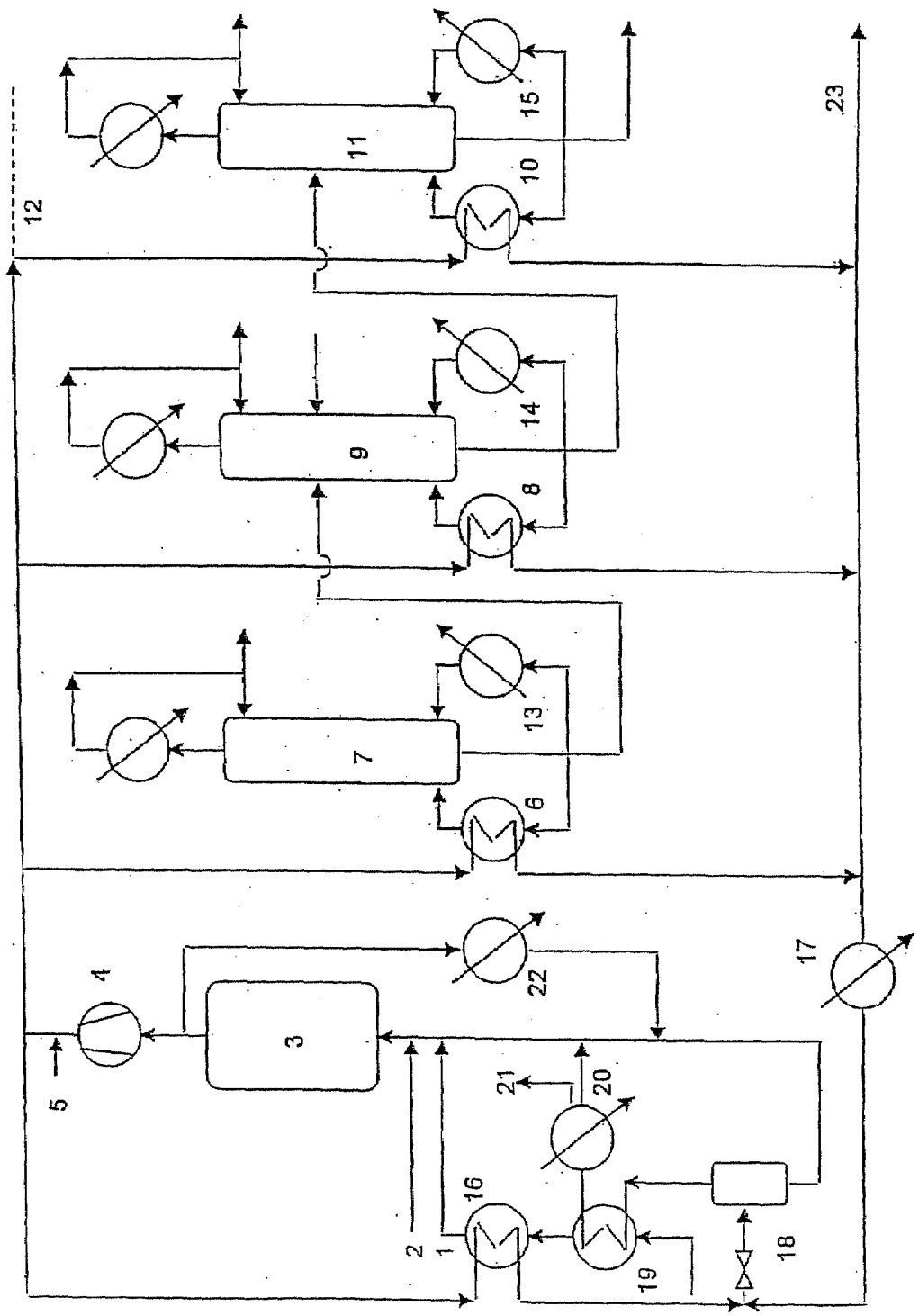
FIG. 1 a typical plant arrangement according to this invention

In the typical arrangement according to FIG. 1, evaporated chlorine gas 1 reacts with ethene 2 in direct chlorination reactor 3 to form EDC. The reaction heat is removed from direct chlorination reactor 3 by the vapours of the evaporating EDC. Said vapours are compressed in compressor 4. The superheat contained in the compressed vapours is dissipated by injecting liquid EDC 5. The compressed and saturated vapours thus heat evaporator 6 of light ends column 7, evaporator 8 of heavy ends column 9, evaporator 10 of vacuum column 11 and/or other heat exchangers 12. During startup or when the operating conditions are unsteady, all columns may also be heated using saturated steam 13, 14, 15. The compressed vapours are also suitable for superheating the evaporated chlorine 16.

Cooling the complete volume of condensed vapours in trimming cooler 17 and flashing device 18 will exactly yield the amount of EDC flash vapour required for heating the chlorine evaporator 19 by condensing said vapour. The uncondensed EDC flash vapour is further condensed in cooling trap 20, leaving a residual portion which primarily consists of inert gases and is routed to outlet 21. This method is applied to separate from the EDC all the barrier gas originating from the shaft seal of the turbo-compressor and contained as impurity in the EDC vapours.

For startup purposes or in the event of unsteady operating conditions, the direct chlorination reactor may also be cooled with cooling water 22. Trimming cooler 17 serves to ensure an equilibrated heat balance. The mass balance is properly maintained by removing EDC product 23 from the fully condensed vapours.

Figure 2:
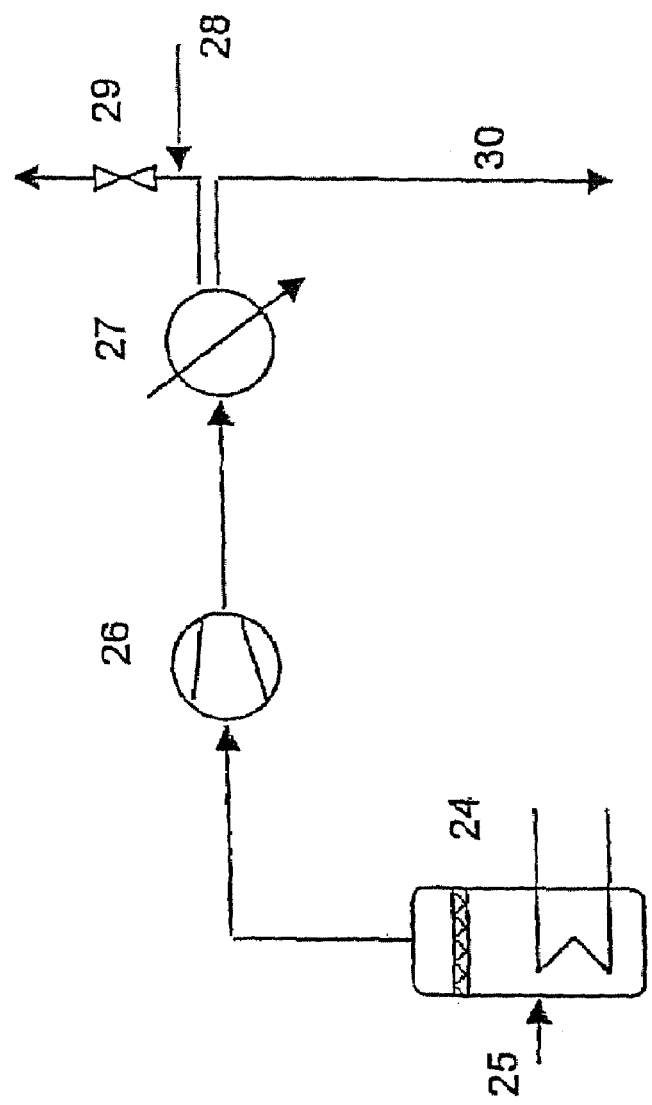
FIG. 2 an equipment configuration for a functional test.

FIG. 2 illustrates a functional test which is also described in patent No. EP 0 180 925 B1, the temperatures being specified in centigrades and the pressure as absolute pressure. ppm by wt. is understood to mean mg of the respective material per kg weight of the EDC fraction. The EDC feedstock as obtained from the vapours originating from a direct chlorination reactor with reduced reaction temperature were specified as follows:

| 99.9 | % by wt. | EDC (1,2-dichloroethane) |
| 260 | ppm by wt. | EDC (1,1-dichloroethane) |
| 490 | ppm by wt. | 1,1,2-trichloroethane |
| 140 | ppm by wt. | hydrogen chloride |
| 110 | ppm by wt. | ethene |

The EDC of the above specification was evaporated in a heated vessel 24, the level in said vessel being kept at a constant value by feeding EDC of the same quality via 25. The evaporation took place at a pressure of 1.3 bars and the corresponding saturated vapour temperature of 92° C. The vapours were compressed by compressor 26 to 3.05 bars at a temperature of 133° C. The vapours superheated by approx. 8 K were fully condensed in condenser 27. A nitrogen blanket 28 downstream of condenser 27 was used for controlling the pressure 29. The specifications of the fully condensed vapours 30 are identical to those of the uncondensed vapours and a comparison of the analyses upstream and downstream of the compressor did not show any difference.

This leads to the conclusion that the ultra-pure EDC obtained from the direct chlorination reactor operated at a reduced temperature level exhibits an even lower tendency to cause post-reactions and the subsequent operational problems with the compressor than the EDC purified in and removed from the head of the distillation column in accordance with the state of the art described in patent no. EP 180 925 B1, a feature which represents a further advantage of the invention.

The invention claimed is:

1. A process for heat recovery in the production of 1,2-dichioroethane from chlorine and ethene by direct chlorination, wherein the vaporous 1,2-dichloroethane obtained from a direct chlorination reactor is compressed without phase change and then fed to heat exchangers for heat recovery.

2. A process according to claim 1, wherein the compressed 1,2-dichioroethane is fed to an evaporator of a light ends dehydration column and/or to an evaporator of a heavy ends column and/or to an evaporator of a vacuum column and/or to a chlorine heater upstream of a direct chlorination reactor.

3. A process according to claim 1 wherein the dehydration column for purifying 1,2-dichloroethane, which is operated at a head pressure of 1.0 to 1.6 bars abs., is heated by providing a heat exchange between the bottom product and the compressed vapors from the direct chlorination reactor at a temperature difference of 8 and 25° C., the bottom temperature being maintained in the range of 80 to 105° C. by an adequate bottom discharge stream.

4. A process according to claim 1, wherein the heavy ends column for purifying 1,2-dichloroethane, which is operated at a head pressure of 0.7 to 1.4 bars abs., is heated by providing a heat exchange between the bottom product and the compressed vapors from the deydration column at a temperature difference of 8and 250° C., the bottom temperature being maintained in the range of 84 to 105° C. by an adequate bottom discharge stream.

5. A process according to claim 1, wherein the vacuum column used for purifying the bottom discharge stream from the heavy ends column and operated at a heat pressure of 0.2 to 0.3 bars abs. is heated by providing a heat exchange between the bottom product and the compressed vapours from the direct chlorination reactor at a temperature difference of 8 and 25° C., the bottom temperature being maintained in the range of 80 to 90° C. by an adequate bottom discharge stream.

6. A process according to claim 1, wherein liquid chlorine used for direct chlorination is evaporated and superheated by heat exchange with the compressed vapors from the direct chlorination reactor or by heat exchange with circulated liquid 1,2-dichloroethane from the direct chlorination reactor.

7. A facility for running the process according to claim 1, wherein a turbo-compressor is used to compress the vaporous 1,2-dichioroethane withdrawn from the direct chlorination reactor.

8. A facility according to claim 7, wherein the turbo-compressor is equipped with a tandem type shaft seal and in that a device is provided for supplying said shaft seal with nitrogen as barrier gas.

9. A facility according to claim 7, wherein a speed controller is provided to adjust the delivery rate of the turbo-compressor to the discharge rate of the direct chlorination reactor.

* * * * *